United States Patent [19]
Selby

[11] Patent Number: 5,526,681
[45] Date of Patent: Jun. 18, 1996

[54] GAS-CONTAINING VESSEL TO ESTABLISH DESIRED HEAT FLUX

[76] Inventor: Theodore W. Selby, 4402 Arbor Dr., Midland, Mich. 48640

[21] Appl. No.: 425,587

[22] Filed: Apr. 20, 1995

[51] Int. Cl.$^6$ .............. F25D 23/06; F25D 1/00; B65D 81/38

[52] U.S. Cl. ............... 73/54.430; 73/54.280; 73/25.010; 73/54.350; 62/383.000; 62/430.000; 62/451.000; 374/33.000

[58] Field of Search ............... 73/54.43, 25.01, 73/25.03, 54.35, 54.28, 54.33; 62/383, 55.5; 374/33.0

[56] References Cited

U.S. PATENT DOCUMENTS

| | | | |
|---|---|---|---|
| 2,801,526 | 8/1957 | Solley, Jr. | 62/6 |
| 3,024,941 | 3/1962 | Vandenberg | 220/63 |
| 3,225,820 | 12/1965 | Riordan | 165/26 |
| 3,654,773 | 4/1972 | White | 62/371 |
| 4,388,814 | 6/1983 | Schilling | 62/62 |
| 5,040,410 | 8/1991 | Chu et al. | 73/54 |

OTHER PUBLICATIONS

ASTM D 2983–87 (Reapproved 1993).
Selby et al., *SAE Transactions*, vol. 68, 1968, pp. 457–467.
Brookfield Viscometers/Rheometers, Catalog, Brookfield Engineering Laboratories, Inc., Stoughton, Mass., 1993, pp. 10–11, 14–15 & 21–22.
Tannas Co., Catalog, Tannas Co., Midland, Mich., 1994, p. 10.

*Primary Examiner*—Hezron E. Williams
*Assistant Examiner*—J. David Wiggins
*Attorney, Agent, or Firm*—Christopher J. Rudy

[57] ABSTRACT

A vessel has a sealable, hollow housing about a sample compartment, and the hollow portion contains a predetermined amount of a gas. It provides for heat transmission control. Accordingly, for an illustrative example, viscosity testing with a sensitive rotating viscometer and an oleaginous sample which is subjected to temperature control can be carried out with high reliability.

20 Claims, 1 Drawing Sheet

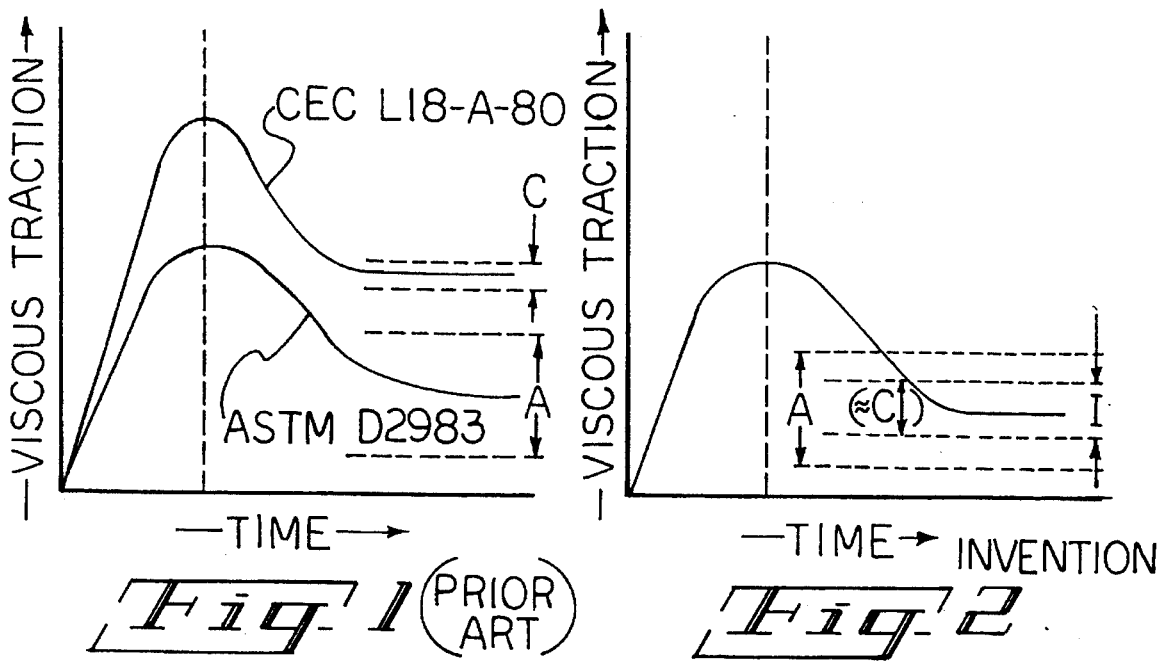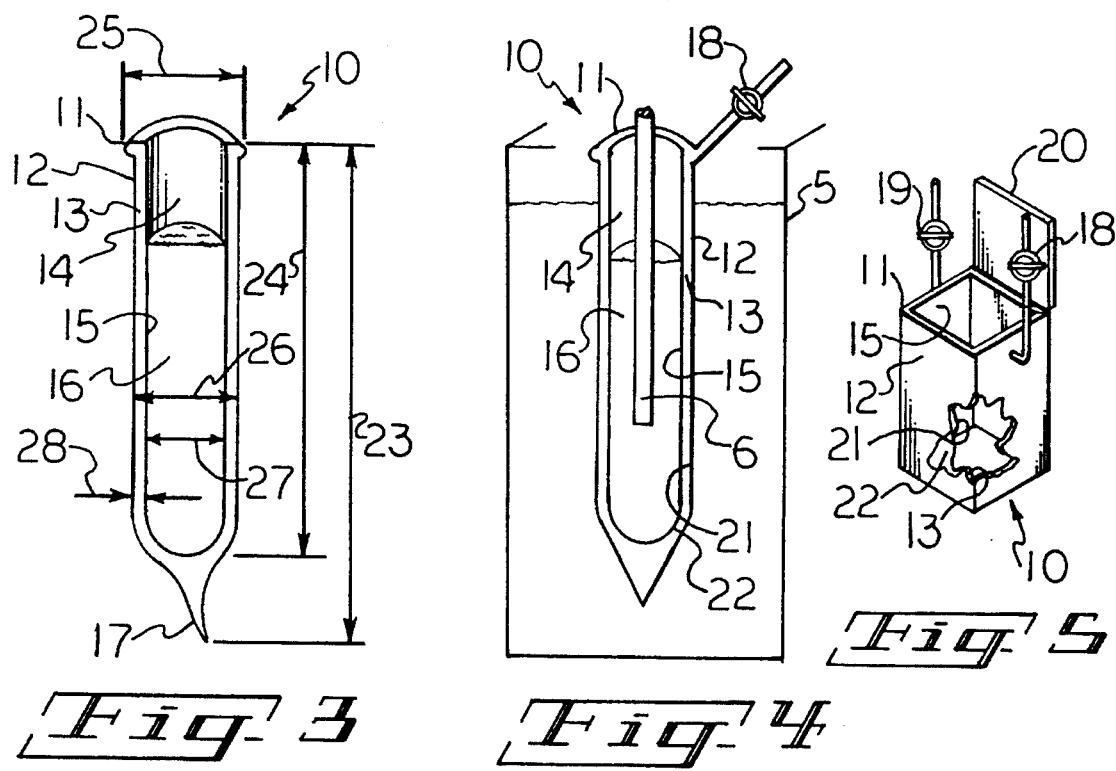

GAS-CONTAINING VESSEL TO ESTABLISH DESIRED HEAT FLUX

FIELD

The present invention concerns heat transmission and its regulation, and apparatus therefor having a sealable or sealed, hollow housing about a sample compartment.

BACKGROUND

Dewar flasks are known apparati having a sealable or sealed, hollow housing, which is evacuated or substantially evacuated through application of as much vacuum as possible. The object of a Dewar flask is to insulate to the fullest extent. Thus, the vacuum is applied rather indiscriminately but so as to provide the lowest pressure inside the housing for the least amount of heat transmission. The Dewar flask is a known, effective insulator to keep substances hot or cold for extended periods, especially for cool materials, and it may be employed as a bath tub in viscosity testing.

In the art of testing oil and related fluid viscosity, one longstanding, well known test protocol is ASTM D 2983, which was developed in the 1950s by Theodore W. Selby. See e.g., *SAE Transactions* 68:457-67, 1960. In the ASTM D 2983 protocol, q.v., a lubricant fluid sample is cooled in an air bath at test temperature for 16 hours. The sample is then carried in an insulated container of balsa wood to a nearby sensitive rotational viscometer such as, for example, a Model LVT or LVTD viscometer available from Brookfield Engineering Laboratories, Inc., Stoughton, Mass., or a Scanning Brookfield PlusTwo (TM) viscometer available from Tannas Co., Midland, Mich., where Brookfield viscosity is measured at a predetermined temperature in the range from minus 5 to minus 40 degrees C. See, FIG. 1. This protocol has a number of disadvantages, to include as follows:

1) Repeatability of cooling of a given sample is not optimum due to the air cooling of samples, etc. Therefore, duplicate or triplicate samples are run to obtain an average value of viscosity in order to reduce inconsistency to some extent.

2) Having to remove the cooled stator tube from the air bath and inserting it into the balsa block for the viscosity measurement interjects an undesired temperature increasing effect on the sample. Since viscosity generally decreases due to the rise in temperature, and a change in a few tenths of a degree in temperature can have a dramatic effect on viscosity, the test can be unreliable.

3) A general plot of the response of a viscometer to a to a fluid versus time would show that initially values shown by the instrument quickly increase to the value reflecting the viscosity because of instrumental factors such as the typical rotational viscometer spring coiling. Next, the values decrease due to non-Newtonian properties of the sample such as shear degradation and gelation plus an increase in temperature. A general plot of viscosity versus temperature would show that the viscosity decreases in a sample as the temperature increases. The magnitude of these competing effects cannot be effectively distinguished thereby.

4) A long time is required to run each test. Not only does sample cooling take the many hours, but time is required to transfer the sample, and to measure its viscosity. For example, 30 seconds is required at 30 or 60 rotations per minute (rpm) for lower viscosity liquids, but 5 minutes is required at 0.6 rpm for higher viscosity liquids with the protocol. The more viscous a liquid is, the more time the test runs take, and these highly viscous liquids are generally of critical import, but their viscosity measurement is of the poorest reliability with such long times required to run the tests, as undesired heating of the sample, etc., occurs.

5) Large numbers of samples in duplicate are required to obtain the viscosity values over a meaningful range of temperature. Another protocol in the viscosity testing art akin to the ASTM D 2983 is the CEC L18-A-80, a European standard. In this European protocol, q.v, a liquid bath is substituted for the ASTM D 2983 air bath. See, FIG. 1. This protocol is not without its disadvantages, some of which follow:

1) Gelation properties are different.

2) Cooled samples are maintained in the liquid.

3) The same results as ASTM D 2983 are not obtained.

SOME DESIRES

Among other desiderata, it is desired to obtain greater precision in test results, especially within the ASTM D 2983 protocol. Greater accuracy is desired in the art as well.

In addition, further desires are extant in the art.

SOME SOURCES OF THE PROBLEMS

On the basis of the foregoing, within the glass stator which is being cooled in the air or liquid bath resides the required thin rotor which is immersed in the lubricant fluid sample, commonly an oil, and it is the sample that is to be cooled. A heat gradient, with isotherms particular to the bath with its heat coefficient, is established, different from the sample, and peculiar to the bath and stator. This makes for different sample profiles, even for the same lubricant in the same test protocol. With a liquid cooling bath, during testing, a flux is maintained which may alter the properties of the sample and interfere with the test results, and the cooling gradient is not duplicatable. What is more, a test protocol may introduce undesired temperature rises in the sample, and viscosity must be measured at constant temperature for accuracy.

SOME OBJECTS

Accordingly, it is an object of the present invention to ameliorate or solve one or more, if not all, of the aforementioned problems.

It is an object of the invention to satisfy some, if not all, of the desires in the art.

It is an object hereof to provide for more uniform cooling of a contained sample.

It is an object hereof to provide for a substantially constant temperature environment and to provide for known or regulatable heat flux with respect to a contained sample.

It is a more particular object hereof to satisfy the foregoing objects in the viscosity testing art.

It is a more particular object hereof to provide for a more precise manner in which viscosity samples are tested.

It is a more particular object of the invention to provide the temperature control available from a liquid bath in a system in which the heat flux is that of a gas.

Additional objects hereof are discernible from a reading of the present specification.

SUMMARY

The present invention provides a vessel useful for heat transmission regulation comprising a sealable, hollow housing about a sample compartment, a hollow portion of said housing containing a predetermined amount of a gas. It thus provides for heat transmission control methodology.

In satisfying one or more if not all of its objects, the invention can meet generally all criteria desired in the art. In particular, as for example in viscosity testing, it can avoid sample cooling variations, loss of temperature control on transfer of a sample from cooling bath to instrument, and confusion of non-Newtonian effects and temperature rise on sample measurements. It can provide for repeatable cooling curves and cooling gradients, and thus result in higher accuracy and precision in sample testing. Moreover, it can provide the temperature control available from a liquid bath in a system in which the heat flux is transmitted through the medium of a gas. The invention is readily made and simple to operate, and adaptable to many fields of endeavor.

Numerous further advantages attend the invention.

DRAWINGS

The drawings form part of the specification hereof. In the drawings, in which like numerals refer to like features, the following is briefly noted:

FIG. 1 (Prior Art) is a general graph of viscous traction versus time of sensitive rotational viscometer test results for ASTM D 2983 and CEC L18-A-80 protocols.

FIG. 2 is a general graph of viscous traction versus time of sensitive rotational viscometer test results of the present invention.

FIG. 3 is a side, cut away view of a vessel for heat transmission regulation of the invention.

FIG. 4 is a side, cut away view of another embodiment of a vessel for heat transmission regulation hereof.

FIG. 5 is a perspective, partial cut away view of another embodiment of a vessel of the present invention.

ILLUSTRATIVE DETAIL

The invention may be further understood with reference to certain illustrative embodiments and the drawings, which are not to be construed as necessarily limiting in nature.

With reference to the drawings, graphs of viscous traction versus time (FIGS. 1 (Prior Art) & 2 (Invention)) show that in the ASTM D 2983 the uncertainty in measured viscosity A is relatively great, but in the CEC L18-A-80 the uncertainty in measured viscosity C is less. However, even though the precision in the CEC L18-A-80 is greater, it suffers from poorer accuracy in relation to the desired value of viscosity as measured by the ASTM D 2983 protocol. In comparison, in the practice of the invention uncertainty in measured viscosity I can be less than A and approximately that of C, but its accuracy does not suffer as it can lie midway in the range of viscosity uncertainty values of A.

Thus, with practice of the present invention in viscosity testing, one can have the best of both worlds, the precision of the CEC L18 -A- 80 protocol plus the accuracy of the ASTM D 2983 protocol. Among other things, this is because gelation and other characteristics of the test fluid such as an oil or transmission fluid remain as affected by a heat flux as provided by a gas environment but the temperature regulation is typically more disciplined.

With further reference to the drawings, vessel for heat transmission regulation 10 has housing 11 of suitable material(s) with external wall 12, internal hollow volume 13, which contains a predetermined amount of gas, say, air at a pressure of 10 to 100 mm Hg. These features are about sample compartment 14, having internal sample compartment wall 15, which can contain sample 16, say, an oleaginous liquid such as an oil, a transmission fluid, and so forth.

In reference to FIG. 3, the vessel 10 is of glass, has sealable, hollow housing 11, external wall 12, and internal wall 15, which are generally cylindrical, and is designed so as to have its sample compartment 14 defined by its internal wall 15 precision engineered for use as a stator in sensitive rotational viscometer viscosity testing. The housing 11 is sealed with seal 17 to permanently contain gas in the hollow volume 13. The seal 17 can be provided by known methodology, as with glass by drawing the same while the glass is hot, say, within a gas environment to match that of the hollow volume 12 at a predetermined pressure.

In reference to FIGS. 4 & 5, the vessel 10 has sealable, hollow housing 11 which is sealed with seal valve 18 to contain gas in the hollow volume 13 for a set period of time. The seal valve 18 is shut when a predetermined amount of gas is filled in or evacuated from the hollow volume 13, and may be opened to alter or change the gas and/or its pressure. As in FIG. 4, the housing 11 may be of glass and the seal valve 18 of glass with a glass or plastic stopcock. As in FIG. 5, purge valve 19 may also be present to assist in changing a gas and/or its pressure, it, for example, being opened with the seal valve 18 when changing the gas identity or flushing the hollow volume 13; external wall 12 may be of glass and internal sample compartment wall 15 of metal, and top closure lid 20 is present. As well, mirrored surface, for example, as provided by a silver coat, may be provided, as on internally, hollow-volume-facing surface 21 of the external wall 12 and/or on internally, hollow-volume-facing surface 22 of the internal wall 15.

In general, as the material for the vessel of the invention, any suitable material may be employed to include glass, metal and/or plastic. Glass and/or metal, as for example, brass or stainless steel, may be advantageously employed. Glass especially is an advantageous material to employ, due to many factors, not the least among which are its formability, inertness, and cost.

As for the size and shape of the vessel of the invention, multifarious sizes and shapes may be employed to advantage. Overall, the vessel may be small to large, to include about from ½ of an inch (ca. 1.27 cm) or less to about 3 feet (ca. 0.914 m) or more, with varying sizes to sample compartment(s) and hollow volume(s) for gas(es). It may be rounded, elliptical, triangular, square, rectangular, trapezoidal, etc., or irregular in general shape, and it may have open or closable sample compartment(s). For example, as in FIG. 3, a generally cylindrical vessel 10 may have an open sample compartment 14 and outside housing height 21 of about 5 inches (ca, 12.7 cm); inside sample compartment height 24 of about 4¼ inches (ca. 10.8 cm); outside top lip diameter 25 of about 1 inch (ca. 2.54 cm); outside barrel diameter 26 of about 15/16 of an inch (ca. 2.38 cm); inside sample compartment diameter 27 of about 13/16 of an inch (ca. 2.06 cm); with an internal hollow volume gap 28 between external and sample compartment walls 12 & 15 of about 1/16 of an inch (ca. 0.16 cm).

As the gas, in addition to air, especially dry air, may be mentioned gases to include, for example, helium, argon, radon, hydrogen, nitrogen, oxygen, carbon dioxide, methane, ethane, propane, methyl chloride, and so forth and the like. A selected gas may be employed singly or in combination with one other gas or two or more other gases.

As for the gas pressure, any suitable pressure may be employed. Advantageously, subatmospheric pressures may be employed, the lower values of such pressures as for ranges of pressure which may be employed may be about 0.1, 0.5, 1, 5, 10, 15, 20, 50, 100 and 200 mm Hg, and upper ranges of pressure, which may be selected independently of the lower values for a range, may be about 700, 500, 300, 100, 75, 50, 30, 20, 10 and 5 mm Hg. Pressures which are about ambient or greater than atmospheric pressure may be employed.

The gas and its accompanying pressure can be selected to provide a known, predetermined value for a heat flux. In this manner, for example, test protocols may be provided with increased parameter stability, which can lead to better test reliability. Also, heat sensitive samples may prepared with precise heat flux parameters.

In use, for example as in FIG. 4, the vessel 10 may be immersed in bath 5 of a gas, e.g., air; liquid, e.g., water, methanol, propanol and dry ice slush, molten Woods metal; or solid, e.g., aluminum, copper, brass, gold, sand, cement; but say, of methanol, and have thin spindle rotor 6 in its sample compartment 14 along with a sample 16 for viscosity testing. The contents of the vessel 10 may be conditioned in the bath for a predetermined period of time, under a known heat flux particular to the vessel 10 and suitable for the desired conditioning and/or testing. Testing may be carried out without moving the vessel 10 from the bath 5, again under the known heat flux particular to the vessel 10.

The invention may be considered to be a modified pressure Dewar flask. That is, a Dewar flask which has been modified to contain a predetermined amount of a select gas.

It is useful not only in sensitive rotational viscosity testing, but also in other fields. For example, it may be advantageously employed in biology in the setting up of precisely formulated agar samples in which the vessels may permit more exact replication of desired parameters. It may be employed to hold a sample at a very precise temperature at a certain regulated heat flux, which may be advantageous in obtaining precise crystal replication. Numerous other applications can be found for the flask of the invention.

The following example further illustrates the present invention and its practice.

EXAMPLE

Tests are conducted according to a protocol analogous to the ASTM D 2983 with various oleaginous liquids as test samples in a glass vessel of the present invention which has an internal volume of reduced pressure air somewhere about 25 mm Hg. See, FIG. 3. However, instead of conditioning of the samples being conducted in an air bath, the glass vessels with samples through the manner of and rotor spindles are conditioned for 16 hours at a specified temperature in a precisely controlled methanol bath, and the samples are tested in the vessels while being yet in the methanol bath under the precise temperature control. Results are obtained, which indicate precision approaching the CEC L18-A-80 protocol within the bounds of accuracy of the ASTM D 2983 protocol. See, FIG. 2.

CONCLUSION

The present invention is thus provided. Numerous modifications can be effected within its spirit, the literal claim scope of which is particularly pointed out as follows:

I claim:

1. A vessel having an inner wall and an outer wall useful for heat transmission regulation comprising a sealable, outer housing placed about a sample compartment with a separation gap spacing disposed therebetween to form a thermal insulation layer around the sample compartment, which defines a hollow portion of the vessel; the hollow portion of the vessel containing a predetermined amount of a gas, without there being present in the hollow portion of the vessel a non-gaseous substance.

2. The vessel of claim 1, wherein the housing has an external wall, and the sample compartment has an internal wall, both walls defining the hollow portion.

3. The vessel of claim 2, wherein the housing, the external wall, and the internal wall are made of glass.

4. The vessel of claim 3, wherein the hollow portion is permanently sealed.

5. The vessel of claim 3, wherein at least one mirrored surface is present on at least one of the outer housing and the sample compartment.

6. The vessel of claim 2, wherein the sample compartment is defined by the inner wall and is precision engineered for use as a stator in sensitive rotational viscometer viscosity testing.

7. The vessel of claim 4, wherein the gas is air.

8. The vessel of claim 4, wherein the gas is a gas other than air.

9. A vessel useful for heat transmission regulation comprising a sealable, outer housing with top, bottom and side portions thereof placed about a sample compartment with a separation gap spacing disposed therebetween to form a thermal insulation layer around the sample compartment at the bottom and sides of the vessel, which outer housing and sample compartment join each other generally only at top portions thereof and define a hollow portion of the vessel; the hollow portion of the vessel containing a predetermined amount of a gas, without there being present in the hollow portion of the vessel a non-gaseous substance; wherein the housing defines an external wall, and the sample compartment defines a generally cylindrical internal wall, both walls defining the hollow portion, and which vessel is further useful in viscosity testing.

10. The vessel of claim 9, wherein the housing, the external wall, and the internal wall are made of glass.

11. The vessel of claim 10, wherein the hollow portion is permanently sealed with the gas being air.

12. The vessel of claim 11, wherein the air is present at a subatmospheric pressure.

13. In a method to test for viscosity of a liquid with a sensitive rotational viscometer having a rotor immersed in a sample of the liquid contained in a stator, wherein the sample is preconditioned with employment of a temperature control environment, the improvement comprising steps of (A) providing the stator in the form of a vessel useful for heat transmission regulation comprising a sealable, hollow housing about a sample compartment, a hollow portion of said housing containing a predetermined amount of a gas, wherein the housing has an external wall, and the sample compartment has a generally cylindrical internal wall, both walls defining the hollow portion;

(B) providing the sample and containing it in the sample compartment of the vessel;

(C) preconditioning the sample while it thus resides in the vessel, (D) and then testing the sample for viscosity with the sensitive rotating viscometer while the sample resides in the vessel.

14. The vessel of claim 1, wherein the predetermined amount of a gas is a gas at about ambient atmospheric pressure.

15. The vessel of claim 14, wherein the gas is air.

16. The vessel of claim 11, wherein the air is present at about ambient atmospheric pressure.

17. The vessel of claim 9, wherein the predetermined amount of a gas is a gas at about ambient atmospheric pressure.

18. The method of claim 13, wherein the predetermined amount of a gas is a gas at about ambient atmospheric pressure.

19. A vessel useful for heat transmission regulation comprising a sealable, hollow housing placed about a sample compartment with a separation gap spacing disposed therebetween to form a thermal insulation layer around the sample compartment, thereby defining a hollow portion of the vessel; a hollow portion of the vessel containing a predetermined amount of a gas; without there being present in the hollow portion of the vessel a non-gaseous substance; wherein the housing defines an external wall, and the sample compartment defines an internal wall, both walls defining the hollow portion and wherein the hollow portion is regulatably sealable by at least one valve.

20. The vessel of claim 19, wherein the housing, the external wall, and the internal wall are made of glass.

* * * * *